United States Patent [19]
Wu

[11] Patent Number: 5,254,235
[45] Date of Patent: Oct. 19, 1993

[54] MICROELECTRODE ARRAYS

[75] Inventor: Huan P. Wu, Beavercreek, Ohio

[73] Assignee: The Yellow Springs Instrument Company, Yellow Springs, Ohio

[21] Appl. No.: 841,843

[22] Filed: Feb. 26, 1992

[51] Int. Cl.$^5$ .................. C25B 11/03; G01N 27/30
[52] U.S. Cl. .................. 204/284; 204/286; 204/400; 204/434
[58] Field of Search .............. 204/416, 418, 419, 400, 204/283, 284, 286, 280, 434

[56] References Cited

U.S. PATENT DOCUMENTS

| | | | |
|---|---|---|---|
| 2,643,223 | 6/1953 | Notvest | 204/284 X |
| 3,154,477 | 10/1964 | Kesler | 204/284 X |
| 3,160,577 | 12/1964 | Nolan, Jr. | 204/284 X |
| 3,329,599 | 7/1967 | Brewer | 204/400 X |
| 3,718,562 | 2/1973 | Haddad | 204/415 |
| 3,926,558 | 12/1975 | Davis | 204/400 X |
| 4,252,627 | 2/1981 | Ohashi et al. | 204/415 |
| 4,263,115 | 4/1981 | Kessler et al. | 204/415 |
| 4,310,400 | 1/1982 | Mark, Jr. et al. | 204/412 |
| 4,753,714 | 6/1988 | Matson | 204/412 X |
| 4,781,798 | 11/1988 | Gough | 204/153.16 |
| 4,820,399 | 4/1989 | Senda et al. | 204/403 |
| 4,839,020 | 6/1989 | Yamaguchi et al. | 204/431 |
| 4,861,454 | 8/1989 | Ushizawa et al. | 204/414 |
| 4,957,615 | 9/1990 | Ushizawa et al. | 204/415 |
| 4,963,245 | 10/1990 | Weetall | 204/403 |
| 4,968,400 | 11/1990 | Shimomura et al. | 204/403 |
| 5,045,163 | 9/1991 | Nyberg et al. | 204/153.1 |
| 5,120,421 | 6/1992 | Glass et al. | 204/418 X |

Primary Examiner—Donald R. Valentine
Attorney, Agent, or Firm—Biebel & French

[57] ABSTRACT

A microelectrode array for use in electroanalytical chemistry in measuring the electrical characteristics of a solution. A microdisk electrode array is formed by sealing a piece of minigrid into an electroinactive embedding material. One end of the embedding material is polished off to expose an array of microdisks which is defined by ends of the minigrid filaments.

23 Claims, 4 Drawing Sheets

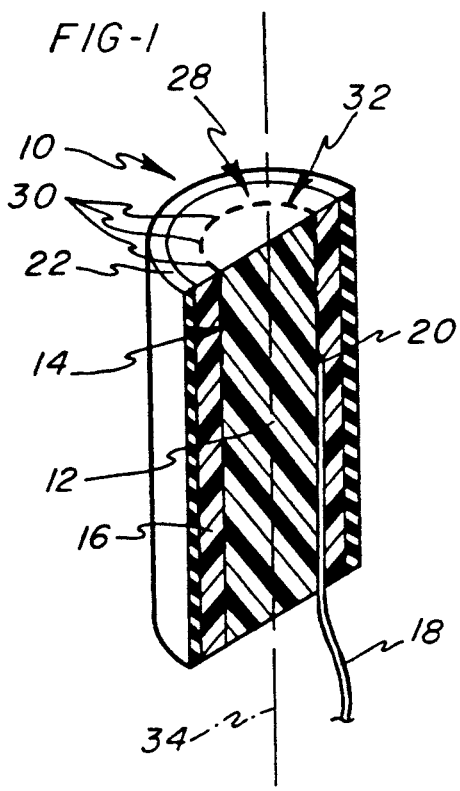
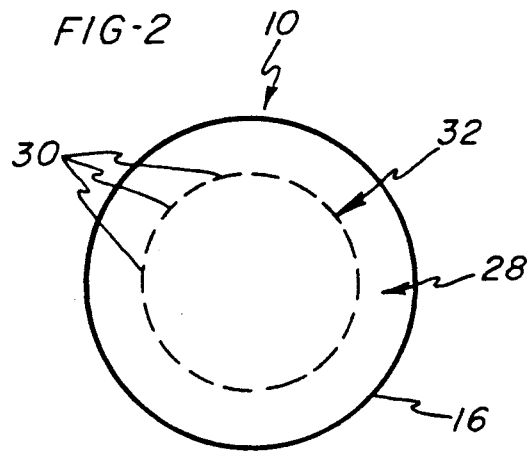
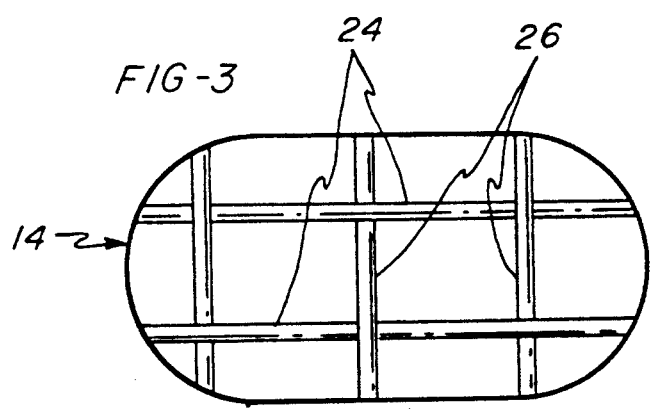
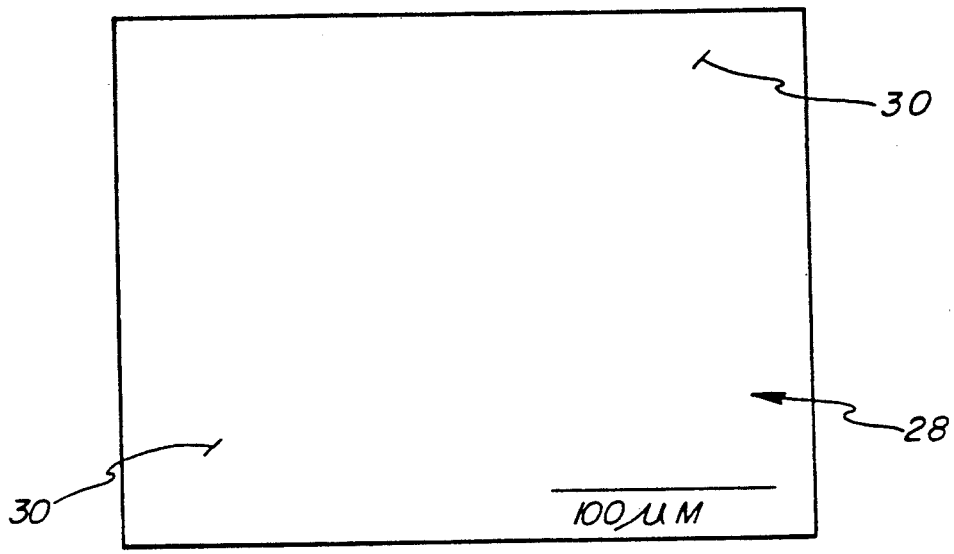

10 μM

MICROELECTRODE ARRAYS

FIELD OF THE INVENTION

This invention relates to microelectrodes which are used in modern electrochemistry. More specifically, this invention relates to the use of minigrids to form a microdisk electrode array for use in electroanalytical chemistry.

BACKGROUND OF THE INVENTION

In modern electrochemistry, microelectrodes have been recognized for their special properties. In particular, the high mass flux at the electrode surface, steady-state current due to three-dimensional diffusion, low cell time constant and low ohmic potential drop properties have made them very attractive for use in electroanalytical chemistry. The major disadvantage in using microelectrodes in electrochemistry is the low current level available therefrom. For example, a microdisk electrode having a 10 micrometer diameter will give a steady-state current of only about 1.5 nanoamps in a solution of 1 mM $Fe(CN)_6^{-3}$.

Currents at these levels are vulnerable to interferences of electrical noise and accordingly require sophisticated measuring instrumentation. This vulnerability can be overcome by the use of microelectrode arrays which maintain the special properties of microelectrodes, but provide an increase in attainable current level.

There have been several attempts to make various kinds of microelectrode arrays. Most of these attempts have compromised the feature of steady-state current.

The failure of most of the attempts to obtain a steady-state current comes from the fact that either the individual electrodes themselves exhibit only virtual steady-state current because of their size, such as microband electrodes, or the disks are randomly dispersed with separations therebetween that are too small causing current shielding.

There have been attempts in using microdisk electrode arrays with relatively large separations between the disks, but this requires handling of individual single microwires in turn causing random separation. Therefore, steady-state current is compromised due to either the large individual electrodes or the small ratio of spacing to disk dimension.

The use of minigrids as an electrode is well-known in the art. For example, the use of a minigrid in an electrode assembly is disclosed in the Senda et al U.S. Pat. No. 4,820,399. A further example of the use of a minigrid as an electrode is disclosed in Mark, Jr. et al U.S. Pat. No. 4,310,400. The Mark device uses a minigrid auxiliary electrode mounted concentric to a thin layer electrode assembly Accordingly, there is a need for a sturdy microelectrode comprising a microdisk electrode array with ordered, relatively large separations between the disks. Further, there is a need for an electrode assembly that can maintain steady-state current at levels in the range of nanoamp or higher to provide adequate measurements for use in electroanalytical chemistry.

SUMMARY OF THE INVENTION

The present invention provides a microelectrode array for performing electrical measurements in electroanalytical chemistry. The microelectrode array incorporates a minigrid which is used to form a microdisk array capable of maintaining a steady-state current and which is supported as a rigid structure for use in electrochemistry applications.

The minigrid forming the microdisk array is positioned within a non-conducting substrate structure having an exposed substantially planar measuring surface defining an end of the electrode. The electrode is preferably formed as a cylindrical element and the minigrid is defined by a plurality of vertical and horizontal conductive filaments woven together wherein the horizontal elements are positioned parallel to the exposed surface of the substrate and the vertical elements extend parallel to the longitudinal axis of the electrode.

During production of the microelectrode array, the ends of the vertical elements are exposed at the measuring end surface of the substrate by grinding away an outer layer of the substrate such that the end-surface and vertical filament ends define a measuring surface for the microelectrode. The ends of the vertical filaments essentially define individual microdisk electrodes and, when taken together, form a microdisk array for the microelectrode of the present invention which provides an increased current measurement over that which would be provided by an individual microdisk electrode.

The minigrid used for the microelectrode is formed of conductive filaments positioned at regularly spaced locations in both the horizontal and vertical directions such that the microdisks formed at the measuring surface are located at locations which are spaced from each other at a predictable predetermined distance, and the horizontal wires provide an electrical contact joining the vertical wires. Thus, the spacing between the microdisks may be selected to minimize adverse effects resulting from overlapping diffusion layer areas surrounding each of the microdisks. In addition, the microelectrode is provided with a conductive wire extending within the substrate and attached to the minigrid in order to convey current produced by the microdisk array to an appropriate measuring instrument.

Therefore, it is an object of the present invention to provide a microelectrode array which provides a higher level of steady-state current.

It is a further object of the present invention to provide a microelectrode with a plurality of microdisks forming an array wherein the microdisks are uniformly spaced to provide a steady-state current.

It is another object of the present invention to provide a plurality of microdisks which are electrically connected.

It is still a further object of the present invention to provide a microelectrode with a microdisk array in which an easily produced rigid structure is provided for holding the microdisk array without handling individual wires.

Yet another object of the present invention is to provide a microelectrode using readily available materials which is relatively easy to construct.

Other objects and advantages of the invention will be apparent from the following description, the accompanying drawings and the appended claims.

BRIEF DESCRIPTION OF THE DRAWINGS

FIG. 1 is a cut-away perspective view of the present invention incorporating a cylindrically shaped minigrid to form a circular microdisk electrode array;

FIG. 2 is an end view of the electrode of FIG. 1 illustrating the positioning of the microdisks;

FIG. 3 is a magnified view of a minigrid used to produce the microdisk electrode array;

FIG. 4 is a magnified view of a section of the microdisk electrode array of FIG. 2 illustrating the relative location of two microdisks;

DETAILED DESCRIPTION OF THE PREFERRED EMBODIMENT

Figure 5:
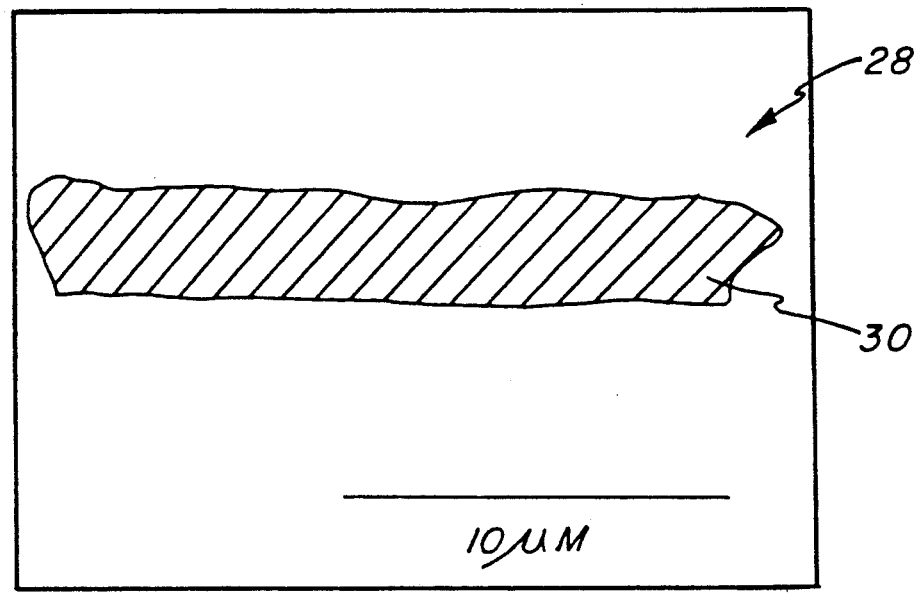
FIG. 5 is a magnified view of a single microdisk as it appears at the end-surface of the electrode of the present invention.

The present invention provides a microelectrode which produces high current levels while retaining the advantages of prior art microelectrodes including the properties of high mass flux, steady-state current, low cell time constant and low ohmic potential drop. The advantages of the present microelectrode array are obtained generally as a result of providing a plurality of microdisks forming an array of sensing surfaces on the electrode measuring surface to thereby provide an increase in the current level produced while retaining the above-noted advantages associated with typical microelectrodes.

Referring to FIG. 1, the electrode 10 of the preferred embodiment of the present invention is illustrated in cut-away form wherein a semi-cylindrical section of the electrode is shown. The electrode 10 includes a precast cylinder 12 formed of an electro-inactive material and a minigrid 14 formed of interwoven horizontal and vertical elements wherein the minigrid 14 is affixed to the precast cylinder 12. The precast cylinder 12 and minigrid 14 are surrounded by a layer of electro-inactive material 16 such as a premixed epoxy which has been cured in place over the cylinder 12 and minigrid 14. A conductive lead wire 18 extends through the outer layer 16 and is attached to the minigrid 14 by a suitable conductive bonding agent 20 such as silver epoxy.

In addition, it should be noted that an outer potting mold or casing 22 is illustrated in FIG. 1 and is used in the manufacture of the electrode. However, the outer casing 22 is typically removed from the completed electrode 10 prior to use.

The precast cylinder 12 and outer layer 16 form a substrate for rigidly supporting the minigrid 14. Further, as was noted above and is illustrated in FIG. 3, the minigrid 14 is formed of a plurality of horizontal filaments or lines 24 which are interwoven with a plurality of vertical filaments or lines 26 to form a substantially rigid structure having regularly spaced conductive elements. The minigrids of the present invention are formed of filaments made from conductive materials such as gold, copper or nickel which may be obtained from Buckbee-Mears of St. Paul, Minn.

FIG. 3 illustrates a minigrid 14 having 90 lines per inch and which has been magnified by 100 times. The typical thickness of the minigrids used in the present invention range from about 3 $\mu$m to 6 $\mu$m. In addition, minigrids 14 appropriate for use in the present invention may range in filament or line density from about 90 lines per inch to 1000 lines per inch, with a maximum line-width of filaments of 20 $\mu$m.

Referring to FIGS. 1 and 2, one edge of the minigrid 14 is exposed at an end or measuring surface 28 of the electrode 10. Further, it should be noted that the horizontal filaments or lines 24 remain embedded within the epoxy layer 16 beneath the measuring surface 28 while end portions of the vertical filaments 26 lie exposed at the measuring surface 28 to form microdisks 30 defining a microdisk array 32. In addition to cooperating with the vertical filaments 26 to maintain the vertical filaments 26 at regularly spaced locations, the horizontal filaments 24 also form conductive paths for electrically connecting the microdisks 30 formed by the various vertical filaments 26.

As a result of the filaments 24, 26 being placed at regularly spaced locations throughout the minigrid 14, the exposed microdisks 30 defined by the filaments 26 are located at regularly spaced locations around the precast cylinder 12. It also should be apparent that it is essential that the vertical filaments 26 be aligned parallel to a longitudinal axis 34 of the electrode 10 in order to insure that no portion of the horizontal filaments 24 will be exposed.

FIG. 4 illustrates a portion of the measuring surface 28 which has been magnified by 400 times showing the relative locations of two microdisks 30 in an electrode 10 which incorporates a minigrid having a filament density of 90 lines per inch. Referring further to FIG. 5, a magnified view (of 5000 times) of one of the microdisks 30 is illustrated showing that the microdisk 30 has a substantially rectangular cross-section resulting from the minigrid 14 being produced from filaments 24, 26 having a rectangular shape. For the purposes of the present invention, reference to the width of a microdisk 30 is directed toward the longest dimension of the microdisk 30, and the maximum width of any one filament is preferably 20 $\mu$m.

It should be noted that the design of the present electrode 10 is particularly advantageous in that it may be produced by a manufacturing method which requires a minimal number of steps while ensuring precise placement of the microdisks 30 relative to each other. Specifically, the above-described electrode 10 may be produced by first wrapping a minigrid 14 around a precast cylinder 12 formed of an electro-inactive material and affixing the grid 14 thereto. In the preferred embodiment, the lower edge of the minigrid 14 is attached to the precast cylinder using Torr Seal which is available from Varian Associates Inc. of Lexington, Mass.

The lead wire 18 is then attached to the minigrid 14 and the minigrid 14 and precast cylinder assembly is positioned within a potting mold such as a piece of heat shrinkable tubing 22. With the precast cylinder 12 centered within the tubing 22, the tubing 22 is filled with a premixed epoxy such as Eccobond 55 sold by W. R. Grace & Company of Woburn, Mass. The epoxy is then cured for at least 8 hours at a temperature ranging from 80° to 85° C. to form a hardened exterior layer 16 around the precast cylinder 12 and minigrid 14. The outer sheath 22 may then be peeled off such that the exterior surface of the electrode 10 is defined by the hard epoxy outer layer 16.

The measuring surface 28 of the electrode 10 is ground or polished to expose the end portions of the vertical filaments 26 of the minigrid 14 to thereby form a plurality of microdisks 30 defining a microdisk array 32 at the surface 28. The microdisks 30 act as a plurality of microelectrodes such that the sum of the currents produced at each of the microdisks 30 will be conveyed by the lead wire 18 to an appropriate measuring instrument.

It should also be noted that the use of the minigrid 14 to provide the individual wire ends at regularly spaced locations around the precast cylinder 12 facilitates production by eliminating the need to handle individual wires forming the individual microdisks 30. Thus, a plurality of filaments forming the microdisks 30 are easily positioned around the precast cylinder 12 during the step of wrapping the minigrid 14 around the cylinder 12.

In addition, the minigrid 14 selected for forming the microdisks 30 may be configured with a larger spacing between the horizontal filaments 24 than between the vertical filaments 26. Such a minigrid configuration provides the desired predetermined spacing between the minidisks 30 formed by the vertical elements 26 while also providing a sufficiently large gap between the horizontal filaments 24 to avoid exposure of a horizontal filaments 24 if the polishing surface is not perfectly parallel to the horizontal filament 24 or if additional material must be removed to form the finished measuring surface 28.

Finally, although a circular array formed by a single minigrid 14 is shown, the array may also be configured as a multicircular array formed of a plurality of minigrids positioned concentrically and electrically connected together.

Figure 6:
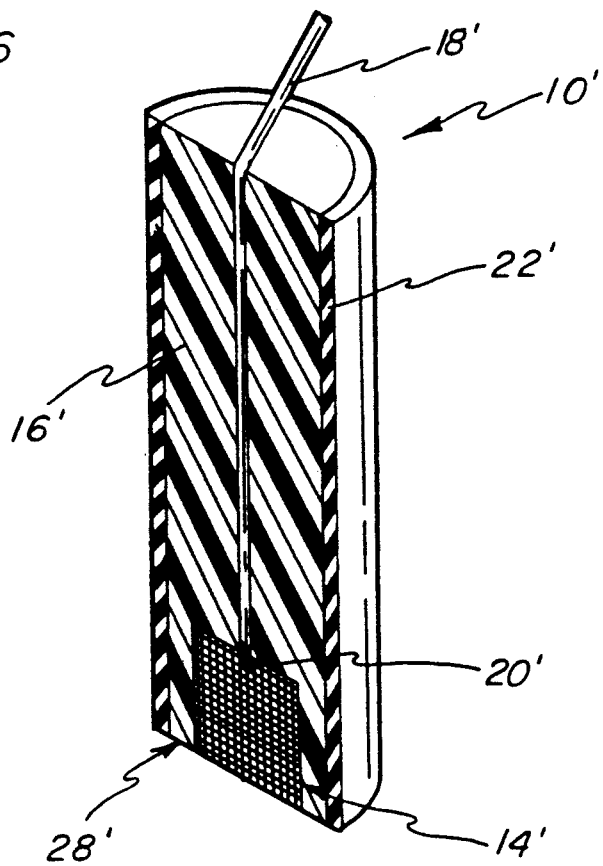
FIG. 6 is a cut-away perspective view of an alternative embodiment of the present invention in which the minigrid forming the electrode array is substantially planar.
Figure 7:
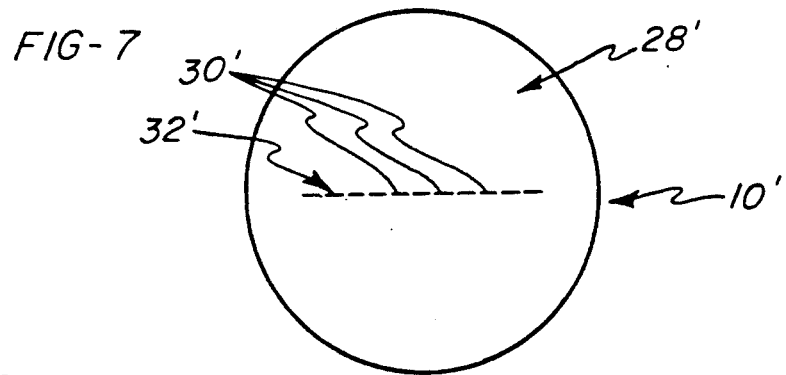
FIG. 7 is an end view of the electrode of FIG. 6 showing the microdisks of this embodiment in a linear array.

FIGS. 6 and 7 illustrate a second embodiment of the invention in which elements similar to those of the first embodiment have been identified with the same reference numeral primed. This embodiment differs from the previous embodiment in that a precast cylinder 12 is not used in the formation of the microdisk array. Rather, a substantially planar minigrid 14' is positioned centered within a potting casing 22' and the casing is filled with an electro-inactive epoxy 16' such that the edge of the substantially planar minigrid 14' defines a line passing through the measuring end surface 28' of the electrode 10'.

As may be seen in FIG. 7, when the end surface 28' of the electrode 10' is polished, the end portions of the minigrid 14' will be exposed to define a linear array 32' of microdisks 30' defined by the end portions of the vertical filaments forming the minigrid 14'. In addition, a plurality of minigrids 14' may be positioned parallel to each other, wherein each minigrid 14' is connected to the lead wire 18', such that a substantially rectangular array of microdisks 30' is defined at the measuring surface 28' by the set of linear arrays.

It should be apparent from the above description of the electrodes 10, 10' of the present invention that the minigrids facilitate construction of the microdisk electrode arrays 32, 32' forming the contact surfaces at the measuring end of the electrodes. Further, the need to handle individual filaments is avoided through use of the minigrids which provide a plurality of regularly spaced filaments which are formed at the measuring surface through a polishing operation exposing the end portions of the vertical filaments 26.

It is important to note that the spacing between the microdisks 30, 30' is a critical aspect of the present invention in assuring that the electrode 10, 10' produces a true steady-state current. Specifically, as the ratio of the spacing between the microdisks to the width of the disks, hereinafter referred to as the d/w ratio, decreases the steady-state performance of the electrode diminishes. This is the result of a current shielding effect which results when an individual microdisk is shielded by adjacent microdisks from drawing a full amount of current due to the overlap of diffusion layers within the solution that the electrode is being used to analyze.

The determination of how much separation between the microdisks 30, 30' is sufficient for an array to have a true steady-state current behavior and the relationship between the current shielding effect and the d/w ratio will be discussed hereafter.

When each microdisk 30, 30' in an array 32, 32' works independently, the total current from an array should be equal to the sum of currents from all microdisks 30, 30'. Since each individual microdisk 30, 30' from the minigrid theoretically has the same surface area, the total current $I_{total}$ from an array of widely separated microdisks 30, 30' should simply be the product of the number of microdisks n and the current $I_o$ for a single microdisk:

$$I_{total} = n \times I_o. \qquad (1)$$

Since the individual microdisks 30, 30' of any given array 32, 32' have the same electrode area and adjacent microdisks 30, 30' are separated by precisely the same distance, it is possible to systematically determine the relationship of the d/w ratio to the current shielding effect. According to equation 1, if the voltammetric current of an array is potted against the number of microdisks 30 30' in an array, the slope should be equal to $I_o$ for a perfect situation where each disk works independently.

Figure 8:
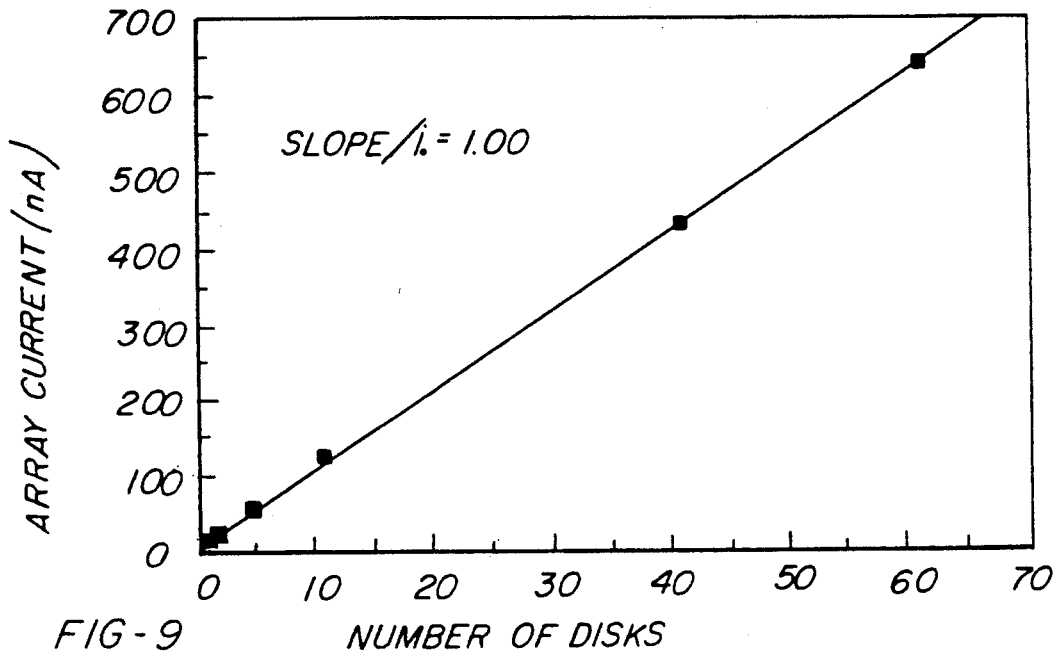
FIG. 8 is a plot of the voltammetric steady-state current at a scan rate of 50 mV/sec versus the number of disks for electrode arrays formed of minigrids having 90 filaments per inch and a maximum microdisk width of 20 $\mu$m.

FIG. 8 illustrates a plot of voltammetric steady-state current produced by various electrode arrays having different numbers of microdisks 30, 30' at the measuring surface 28, 28'. Each of the electrodes used for the plot of FIG. 8 was constructed using a minigrid having 90 lines or filaments per inch and having a d/w ratio of 14.4. This plot was obtained using a scan rate of 50 mV/sec and the slope of this plot is equal to $I_o$, which is the current produced by a single microdisk 30, 30'.

Figure 9:
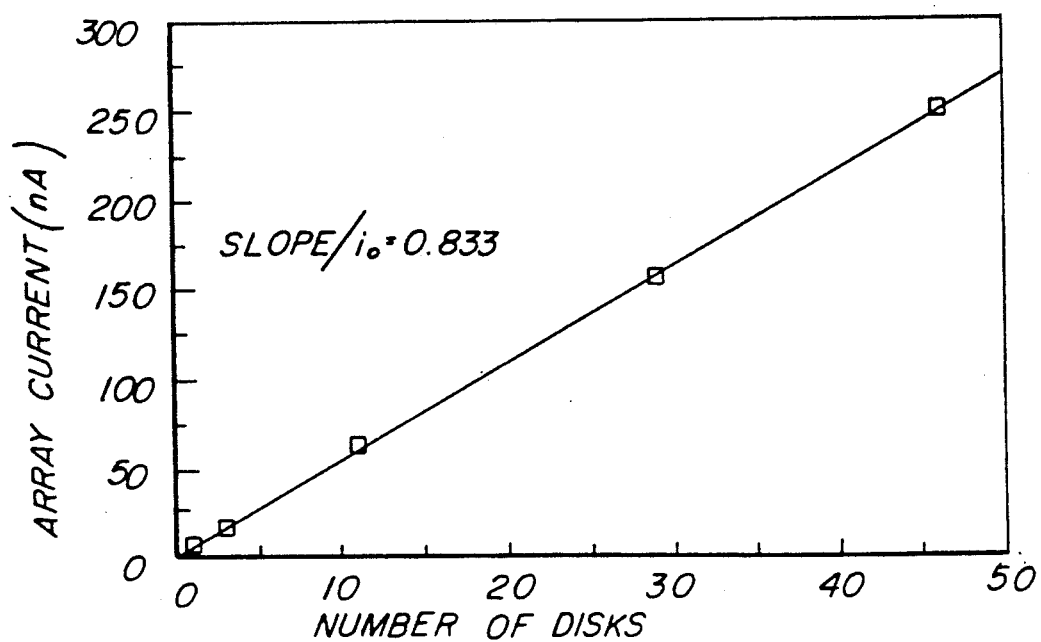
FIG. 9 is a plot similar to the one shown in FIG. 8 in which the electrode arrays are formed of minigrids having 1000 filaments per inch and a maximum microdisk width of 10 $\mu$m.

FIG. 9 is shown for comparison purposes and illustrates a plot similar to that of FIG. 8. The plot of FIG. 9 was obtained using electrode arrays which incorporated minigrids having a filament density of 1000 lines or filaments per inch and in which the d/w ratio was 1.54. It can be seen that the slope for this plot, which was also obtained at a scan rate of 50 mV/sec, is less than $I_o$. The slope I' of this plot is equal to the average current produced by an individual microdisk in the array. The value of $I'$ is a fraction of the current $I_o$ which would be produced by a single microdisk if it were used apart from the other microdisks in the array. The decrease in the average current produced by the individual disks of the array is due to the current shielding effect resulting from the overlap of diffusion layers surrounding each individual microdisk, which overlap of diffusion layers prevents any one microdisk from producing a full current $I_o$ from the solution. In such a case, the total current will not be a multiple of the single microdisk current $I_o$, but rather a multiple of $I'$. Therefore, the current shielding constant can be expressed as:

$$f = I'/I_o \quad (2)$$

The total voltammetric current of an array can be expressed by the following equation:

$$I = n \times f \times I_o \quad (3)$$

When constant f is less than one, an individual disk is shielded by adjacent disks from producing a full amount of current due to the overlap of diffusion layers. No current shielding exists in the array when f is equal to 1. Since a voltammetric test is essentially a time-dependent test, the overlap of diffusion layers and the current shielding effect depends upon how fast the test is performed. In other words, the diffusion characteristics of the individual disks in these arrays will depend on the scan rate used during a particular voltammetric test.

Figure 10:
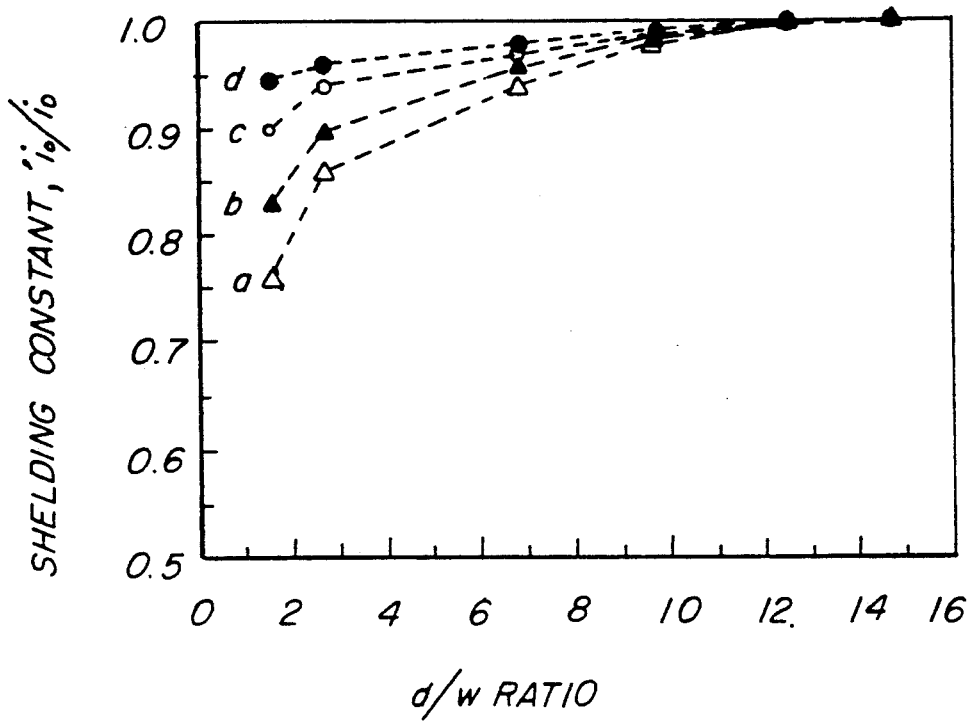
FIG. 10 is a graph of the current shielding constants plotted against the spacing-to-width ratio of microdisk arrays at four different scan rates of (a) 10 mV/sec, (b) 50 mV/sec, (c) 200 mV/sec, and (d) 500 mV/sec.

FIG. 10 illustrates the relationship between the current shielding effect and the d/w ratio in which plots were produced using the following scan rates: (a) 10 mV/sec, (b) 50 mV/sec, (c) 200 mV/sec, and (d) 500 mV/sec. The points used for plotting the lines in FIG. 10 were developed by testing individual electrode arrays having different d/w ratios and for the purposes of this plot, 6 electrode arrays having different microdisks were used. The shielding constant for each of the particular scan rates at each particular d/w ratio is derived by extracting the slopes from plots relating the array current to the number of microdisks, such as those shown in FIGS. 8 and 9.

Referring to FIG. 10, it should be noted that only those arrays with a current shielding constant close to 1 will demonstrate a voltammetric steady-state current, and that the preferred d/w ratio for any array operating at any scan rate is 14.4 or greater.

Figure 11:
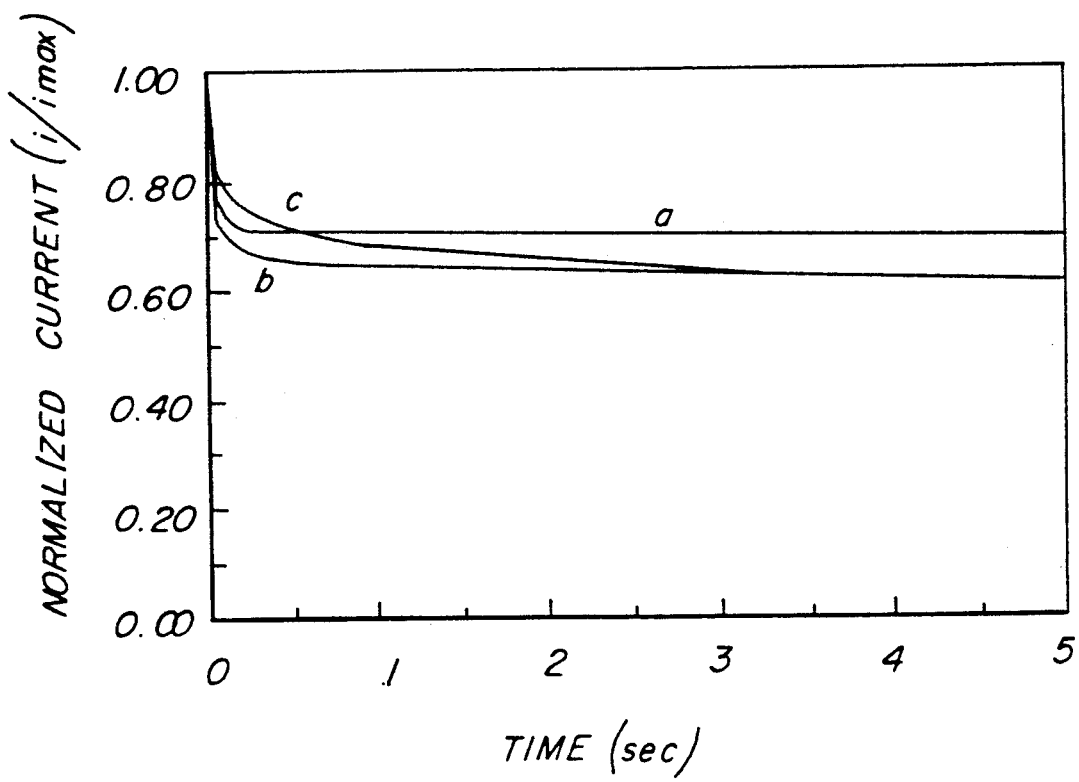
FIG. 11 is a plot of chronoamperomograms produced by three different microdisk electrode arrays of (a) 90 filaments per inch, (b) 200 filaments per inch, and (c) 1000 filaments per inch.

In order to demonstrate further the dependency of current behavior on the d/w ratio, chronoamperomograms (which is the current recorded as a function of time when the electrode potential is held at either an oxidizing or a reducing potential) from three different arrays were determined and are plotted in FIG. 11. Each time function is normalized to its highest current value and therefore the general shapes of each current-time function are illustrated in this figure.

Curve (a) in FIG. 11 is obtained from an array having 90 filaments or lines per inch and shows an almost time-independent current behavior. Curve (b) was produced using a 200 filament per inch minigrid and shows a slowly decaying behavior. The array used for producing curve (b) had a d/w ratio of 6.8 and therefore was subject to overlap of the diffusion layers resulting in a decrease of the average current produced by each microdisk.

Finally, curve (c) in FIG. 11 illustrates a plot produced using a minigrid having 1000 filaments per inch.

It should be noted that curve (c) is drastically different from curves (a) and (b) as a result of the minigrid with a smaller d/w ratio and filaments having a smaller cross-sectional area than those of the arrays having 90 and 200 filaments per inch. Thus, the charging current transient and the linear diffusion transient for the 1000 filament per inch minigrid is faster than the transients for the previous two arrays, permitting the individual disks of the 1000 filament per inch in an array to approach a steady-state current at a faster rate individually. Although the array of curve (c) has a tendency to approach steady-state at a faster rate as a result of the faster approach at each disk, this tendency is hindered by diffusion layer overlap due to a small d/w ratio, which diffusion layer overlap becomes more severe as the testing time passes. The net result of the above-noted effects is an earlier bending and faster decaying behavior of the current-time function.

Thus, it is preferred when constructing a microelectrode incorporating a microdisk electrode array to use a minigrid having less than 200 filaments or lines per inch such that the d/w ratio is greater than 7, and best with the d/w ratio greater than 14. Furthermore, the use of a microdisk array as a microelectrode provides a true steady-state current which is desired in the electroanalytical chemistry. An example of the application of the present invention can be found in the field of sensor technology where the steady-state current reading from an amperometric transducer is desired.

While the forms apparatus herein described constitute preferred embodiments of the invention, it is to be understood that the invention is not limited to these precise forms of apparatus, and that changes may be made therein without departing from the scope of the invention which is defined in the appended claims.

What is claimed is:

1. A microelectrode array for use in electrochemical analysis, comprising:
    a conductive minigrid having a plurality of vertical filaments and a plurality of horizontal filaments woven together, said minigrid having a measuring end;
    means for mounting said minigrid defining a measuring surface; and
    wherein said horizontal filaments of said minigrid are disposed essentially parallel to said measuring surface and said vertical filaments of said minigrid are disposed essentially perpendicular to said measuring surface, and said measuring end of said minigrid is located adjacent said measuring surface such that said measuring end of said minigrid forms an array of discrete conductive surfaces defined by end portions of said vertical filaments of said minigrid.

2. The microelectrode according to claim 1 wherein said array is linear.

3. The microelectrode according to claim 1 wherein said array is rectangular.

4. The microelectrode according to claim 1 wherein said array is circular or multicircular.

5. The microelectrode according to claim 1 wherein said minigrid has a filament density of approximately 10 to 1000 filaments per inch.

6. The microelectrode according to claim 1 wherein the ratio of the spacing of said vertical filaments to the width of said vertical filaments in said minigrid is greater than 7.

7. The microelectrode according to claim 1 wherein said vertical and horizontal filaments of said minigrid are metal wires.

8. The microelectrode according to claim 1 wherein said vertical filaments have a maximum width dimension greater than 1 μm but less than 20 μm.

9. The microelectrode according to claim 1 wherein the spacing between said horizontal filaments is greater than the spacing between said vertical filaments.

10. A microelectrode for use in electrochemical analysis, comprising:

a minigrid having a plurality of vertical filaments and a plurality of horizontal filaments woven together, each said vertical filament defining a measuring end;

mounting means for supporting said minigrid, said mounting means defining a measuring surface, encasing means for encasing said minigrid and said mounting means; and wherein said horizontal filaments are disposed parallel to said measuring surface and said vertical elements are disposed perpendicular to said measuring surface and said minigrid is located between said mounting means and said encasing means.

11. The microelectrode according to claim 10 wherein each measuring end is located adjacent to said measuring surface to define a plurality of discrete conductive surfaces.

12. The microelectrode according to claim 10 wherein said encasing means defines a surface which is coplanar with said measuring surface.

13. The microelectrode according to claim 12 wherein said measuring ends of said vertical filaments are coplanar with said measuring surface and define an array of microdisk electrodes.

14. The microelectrode according to claim 13 wherein said array of microdisk electrodes is linear.

15. The microelectrode according to claim 13 wherein said array of microdisk electrodes is rectangular.

16. The microelectrode according to claim 13 wherein said array of microdisk electrodes is circular or multicircular.

17. The microelectrode according to claim 10 wherein said minigrid has approximately 90 filaments per inch.

18. The microelectrode according to claim 10 wherein the ratio of the spacing of said filaments to the width of said filaments in said minigrid is approximately 14.

19. The microelectrode according to claim 10 wherein said vertical and horizontal filaments of said minigrid are metal wires.

20. The microelectrode according to claim 10 wherein said vertical and horizontal filaments have a maximum width dimension greater than 1 μm but less than 20 μm.

21. A microdisk electrode array for use in electrochemical analysis of solutions, comprising:

a cylinder formed of a precast electro-inactive material, said cylinder having a substantially planar end defining a measuring surface, a minigrid having a plurality of vertical filaments and a plurality of horizontal filaments woven together, said minigrid extending around said precast cylinder and having a measuring end located adjacent to said measuring surface and a coupling end distal from said measuring surface, said measuring end defining a circular array of discrete contact surfaces;

a conductive wire for receiving the electrical signals from said minigrid;

means for coupling said conductive wire to said coupling end of said minigrid; and an encasing layer of electro-inactive material encasing said minigrid and said cylinder, said encasing layer extending from said measuring surface toward said coupling end of said minigrid.

22. The electrode according to claim 21 wherein said electro-inactive material of said cylinder and said encasing layer are both formed of an epoxy material.

23. The electrode according to claim 21 wherein said minigrid has approximately 90 filaments per inch.

* * * * *